(12) United States Patent
Kamradt

(10) Patent No.: US 11,779,722 B2
(45) Date of Patent: *Oct. 10, 2023

(54) TRACHEOSTOMA VALVE

(71) Applicant: Brian Kamradt, Indianapolis, IN (US)

(72) Inventor: Brian Kamradt, Indianapolis, IN (US)

( * ) Notice: Subject to any disclaimer, the term of this patent is extended or adjusted under 35 U.S.C. 154(b) by 218 days.

This patent is subject to a terminal disclaimer.

(21) Appl. No.: 17/335,884

(22) Filed: Jun. 1, 2021

(65) Prior Publication Data

US 2021/0393910 A1    Dec. 23, 2021

Related U.S. Application Data

(63) Continuation of application No. 16/559,575, filed on Sep. 3, 2019, now Pat. No. 11,020,556, which is a continuation of application No. 15/530,923, filed on Mar. 24, 2017, now Pat. No. 10,398,865.

(51) Int. Cl.
*A61M 16/00* (2006.01)
*A61M 16/04* (2006.01)
*A61M 16/08* (2006.01)
*A61M 16/10* (2006.01)
*A61M 16/20* (2006.01)
*F16K 7/14* (2006.01)

(52) U.S. Cl.
CPC .... *A61M 16/0468* (2013.01); *A61M 16/0816* (2013.01); *A61M 16/1045* (2013.01); *A61M 16/201* (2014.02); *F16K 7/14* (2013.01)

(58) Field of Classification Search
CPC ............ A61M 16/0468; A61M 16/201; A61M 16/0816; A61M 16/1045; F16K 7/14
See application file for complete search history.

(56) References Cited

U.S. PATENT DOCUMENTS

| | | | |
|---|---|---|---|
| 4,325,366 | A | 4/1982 | Tabor |
| 4,538,607 | A | 9/1985 | Saul |
| 5,059,208 | A | 10/1991 | Coe et al. |
| 5,738,095 | A | 4/1998 | Presson |
| 8,678,005 | B2 | 3/2014 | Dawson |
| 67,899,542 | | 9/2014 | Bischoff |
| 9,216,263 | B2 | 12/2015 | Root |
| 9,364,630 | B2 | 6/2016 | Bare |
| 2016/0242900 | A1 | 8/2016 | Fahl |

*Primary Examiner* — Steven O Douglas
(74) *Attorney, Agent, or Firm* — Reichel Stohry Dean LLP; Mark C. Reichel; Natalie J. Dean

(57) ABSTRACT

A tracheostoma valve to be applied to a tracheostomized person's neck comprises an air passage to be connected with the tracheostoma for connecting the trachea with the surroundings. A valve member is provided in the air passage, wherein the valve member is normally open and allows for inhalation and exhalation through the air passage. The valve further comprises a manually activated member for establishing an uninterrupted seal to block patient exhalation, thereby to direct it to the patient's pharynx, esophagus, sinuses, and mouth for speech following surgical removal of the larynx.

18 Claims, 4 Drawing Sheets

TRACHEOSTOMA VALVE

PRIORITY

The present application is related to, claims the priority benefit of, and is a U.S. continuation patent application of, U.S. patent application Ser. No. 16/559,575, filed Sep. 3, 2019 and issued as U.S. Pat. No. 11,020,556 on Jun. 1, 2021, which is related to, claims the priority benefit of, and is a U.S. continuation patent application of, U.S. patent application Ser. No. 15/530,923, filed Mar. 24, 2017 and issued as U.S. patent Ser. No. 10/398,865 on Sep. 3, 2019. The contents of each of the aforementioned patent applications are hereby incorporated into the present application directly and by reference in their entirety.

TECHNICAL FIELD

The invention relates to a tracheostoma valve adapted to control the flow of air through a tracheostoma.

BACKGROUND OF THE INVENTION

Due to decreases of different kinds it is sometimes necessary to remove the larynx by surgery and to open a tracheostoma in order that the individual exposed to the surgery can breathe. By the removal of the larynx the ability to speak will be lost but can be restored to some extent by means of another surgery wherein a fistula is opened between trachea and esophagus to pass air to the oral cavity via the fistula. A one-way valve is mounted in the fistula. This valve referred to as a voice prosthesis, allows air to pass from trachea to esophagus but blocks complete flow in the opposite direction. For speech to be generated the tracheostoma must be closed so that air can be passed from trachea via the voice prosthesis into the esophagus and to the mucous membranes of which are made to vibrate so that speech is produced. The tracheostoma can be closed by covering the tracheostoma with a finger but it is more convenient to use for this purpose, a tracheostoma valve of the kind referred to above, which is attached to the neck of the person that has been exposed to tracheostoma surgery, in order to control the connection between trachea and the ambient atmosphere via the tracheostoma. The tracheostoma valve provides manual control of said connection. Embodiments of such valves are disclosed in U.S. Pat. Nos. 5,738,095, 5,059,208, and 4,325,366. The drawback of these valves are of a mechanically complicated and costly construction and moreover often are not attractive aesthetically due to the dimensions thereof which make it difficult to conceal the valves under garments.

SUMMARY OF THE INVENTION

It is an object of the present invention to provide a tracheostoma valve which manually activated will establish an uninterrupted seal to block patient exhalation, thereby to direct it to the patient's pharynx, esophagus, and mouth for speech following surgical removal of the larynx. It is a further object of the present invention to provide a tracheostoma valve which is of mechanically simple construction, in particular to permit ease of operation by a user and/or ready cleaning and/or to reduce costs to such an extent that the valve or components thereof are disposable and replaceable. It is a further object of the present invention to provide a tracheostoma valve of a low profile construction and can be concealed under garments. Further advantageous features of the tracheostoma valve of the invention are defined in the dependent claims.

DETAILED DESCRIPTION

Figure 1:
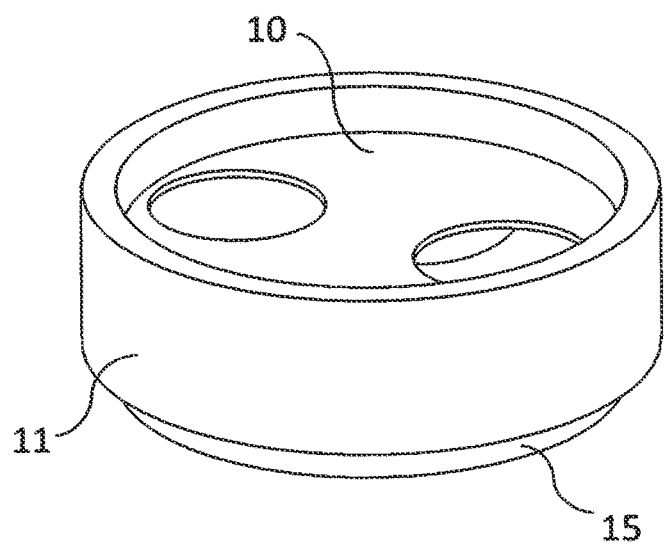
FIG. 1 is a representation of the Tracheostoma Valve with a heat and moisture exchange (HME) unit.
Figure 2:
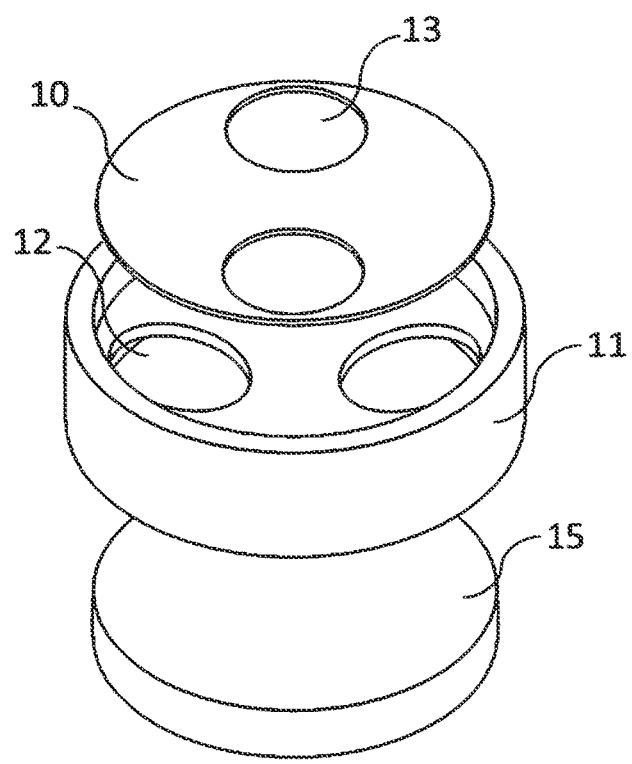
FIG. 2 is an exploded view of the Tracheostoma Valve with HME unit.
Figure 3:
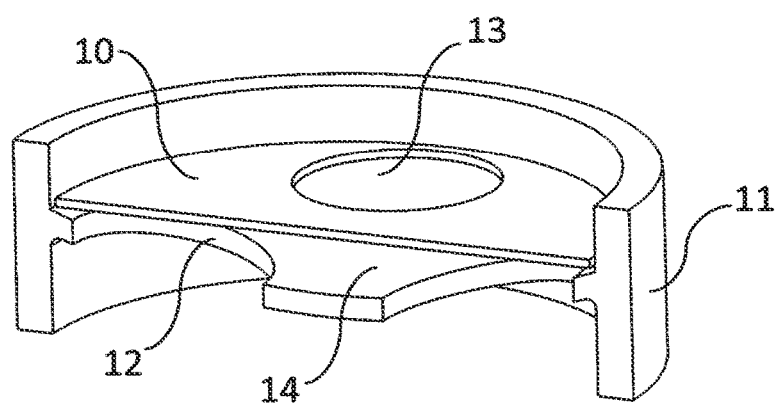
FIG. 3 is a section view of the Tracheostoma Valve in open position.
Figure 4:
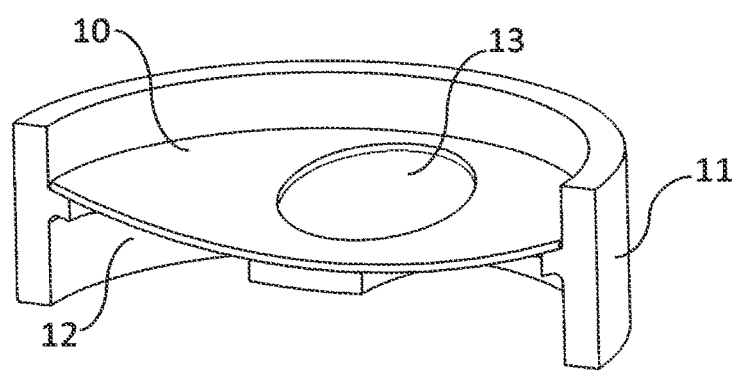
FIG. 4 is a section view of the Tracheostoma Valve in closed position.

The tracheostoma valve disclosed in the drawing comprises a housing 11 which is circular and having an open proximal and distal end and inside concave wall 14 positioned perpendicular to the axis which can be made of plastic material. Said inside concave wall 14 has openings therein 12 allowing air to pass there through. A displaceable member 10 which can be made of a thin resilient plastic sheet material has a disc and bowtie or hourglass shape and is located above said housing concave wall. Said displaceable member has openings therein 13 and are oriented at 90 degrees with respect to that of the openings in said housing concave wall allowing air to pass there through. The valve is combined with a heat and moisture exchange unit (HME unit). The HME unit is a plastic foam body 15 with open cells. The foam body is located and held in place inside the proximal end of the housing 11. The housing further includes a retaining cross bar (not shown) to position and hold the HME unit in a desired position. The proximal end of the housing is intended to be connected to an adapter on a self-adhesive plaster to be attached to the person's neck over the tracheostoma, or to a laryngectomy tube or tracheal cannula to be inserted into trachea through the tracheostoma.

The valve is of the normally open type. To close, the displaceable member 10 is pressed with a finger inward so as to engage the surface of the housing concave wall 14 creating a seal as both displaceable member openings 13 and housing concave wall openings 12 are closed and air is not allowed to pass there through. A rib (not shown) is further provided above the displaceable member to prevent unintended closing of the valve. To open, the finger is removed from the displaceable member to allow it to return to the normal open state allowing air to pass there through. It is further contemplated that the housing further includes a retaining groove (not shown) to position and hold the displaceable member in a desired position.

During breathing inhalation air passes from the ambient atmosphere through the openings 12,13 and through the HME unit 15 into trachea and then to the lungs. During expiration the breathing air follows the same path in the opposite direction. However, if the person wishes to produce speech by passing expiration air through a voice prosthesis the displaceable member 10 is pressed with a finger inward to engage the surface of the housing concave wall 14, both displaceable member openings 13 and housing concave wall openings 12 are closed and no expiration air can pass through the tracheostoma valve to the ambient atmosphere; the air will instead be passed through the voice prosthesis to the oral cavity and from there through the mouth to the ambient atmosphere.

The invention claimed is:

1. A tracheostoma valve, comprising:
   a circular housing having an inside concave wall having openings defined therein allowing air to pass therethrough; and
   a displaceable member comprising a thin resilient material and located relative to said concave wall of the circular housing, the displaceable member having openings defined therein allowing air to pass therethrough that are oriented at or about 90 degrees relative to the openings in concave wall.

2. The tracheostoma valve of claim 1, further comprising:
   a heat and moisture exchange (HME) unit configured to fit within an open proximal end of the circular housing.

3. The tracheostoma valve of claim 2, wherein the HME unit comprises a plastic foam body with open cells.

4. The tracheostoma valve of claim 1, wherein the inside concave wall has two openings defined therein, and wherein the displaceable member has two openings defined therein.

5. The tracheostoma valve of claim 1, having a native open configuration so that air can pass through the openings of the concave wall and the openings of the displaceable member.

6. The tracheostoma valve of claim 1, configured to have a closed configuration so that air cannot pass through the openings of the concave wall and the openings of the displaceable member when the displaceable member is pressed against the inside concave wall of the circular housing.

7. The tracheostoma valve of claim 1, configured for placement over a tracheostoma of a person and operable to control the flow of air therethrough.

8. The tracheostoma valve of claim 1, wherein the displaceable member is configured to be pressed inward to create a seal as the displaceable member openings and the housing concave wall openings are closed and air is not allowed to pass therethrough.

9. A method, comprising:
   positioning the tracheostoma valve of claim 1 over a tracheostoma of a person; and
   inhaling atmospheric air through the tracheostoma valve and into the tracheostoma;
   wherein the step of inhaling is performed by the person.

10. The method of claim 9, further comprising:
    exhaling air through the tracheostoma and out of the tracheostoma valve.

11. The method of claim 9, further comprising:
    pressing the displaceable member to prevent air from flowing through the tracheostoma valve.

12. The method of claim 11, wherein the step of pressing is performed by the person.

13. The method of claim 11, further comprising:
    producing speech while the displaceable member is pressed.

14. A method, comprising:
    positioning the tracheostoma valve of claim 3 over a tracheostoma of a person; and
    inhaling atmospheric air through the tracheostoma valve and into the tracheostoma;
    wherein the step of inhaling is performed by the person.

15. The method of claim 14, further comprising:
    exhaling air through the tracheostoma and out of the tracheostoma valve.

16. The method of claim 14, further comprising:
    pressing the displaceable member to prevent air from flowing through the tracheostoma valve.

17. The method of claim 16, wherein the step of pressing is performed by the person.

18. The method of claim 16, further comprising:
    producing speech while the displaceable member is pressed.

* * * * *